(12) United States Patent
Kim et al.

(10) Patent No.: US 11,975,037 B2
(45) Date of Patent: May 7, 2024

(54) COMPOSITION FOR PREVENTING, ALLEVIATING OR TREATING BURNOUT SYNDROME

(71) Applicant: AMOREPACIFIC CORPORATION, Seoul (KR)

(72) Inventors: Su-Hwan Kim, Yongin-si (KR); Chan-Woong Park, Yongin-si (KR); Sun Mi Kim, Yongin-si (KR); Juewon Kim, Yongin-si (KR); Byung Gyu Kim, Yongin-si (KR); Wan Gi Kim, Yongin-si (KR); Sang Jun Lee, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 341 days.

(21) Appl. No.: 15/549,954

(22) PCT Filed: Feb. 5, 2016

(86) PCT No.: PCT/KR2016/001326
§ 371 (c)(1),
(2) Date: Aug. 9, 2017

(87) PCT Pub. No.: WO2016/129902
PCT Pub. Date: Aug. 18, 2016

(65) Prior Publication Data
US 2018/0028584 A1    Feb. 1, 2018

(30) Foreign Application Priority Data
Feb. 13, 2015    (KR) .................. 10-2015-0022355

(51) Int. Cl.
*A61K 36/258* (2006.01)
*A23L 33/00* (2016.01)
*A23L 33/105* (2016.01)
*A23L 33/15* (2016.01)
*A23L 33/16* (2016.01)
*A61K 31/07* (2006.01)
*A61K 31/122* (2006.01)
*A61K 31/197* (2006.01)
*A61K 31/353* (2006.01)
*A61K 31/355* (2006.01)
*A61K 31/375* (2006.01)
(Continued)

(52) U.S. Cl.
CPC .......... *A61K 36/258* (2013.01); *A23L 33/105* (2016.08); *A23L 33/15* (2016.08); *A23L 33/16* (2016.08); *A23L 33/30* (2016.08); *A61K 31/07* (2013.01); *A61K 31/122* (2013.01); *A61K 31/197* (2013.01); *A61K 31/353* (2013.01); *A61K 31/355* (2013.01); *A61K 31/375* (2013.01); *A61K 31/455* (2013.01); *A61K 31/51* (2013.01); *A61K 31/519* (2013.01); *A61K 31/525* (2013.01); *A61K 31/675* (2013.01); *A61K 31/704* (2013.01); *A61K 31/7048* (2013.01); *A61K 33/00* (2013.01); *A61K 33/06* (2013.01); *A61K 33/26* (2013.01); *A61K 33/30* (2013.01); *A61K 33/42* (2013.01); *A61K 35/32* (2013.01); *A61K 36/232* (2013.01); *A61K 36/40* (2013.01); *A61K 36/534* (2013.01); *A61K 36/54* (2013.01); *A61K 36/64* (2013.01); *A61K 36/725* (2013.01); *A61K 36/79* (2013.01); *A23V 2002/00* (2013.01)

(58) Field of Classification Search
None
See application file for complete search history.

(56) References Cited

U.S. PATENT DOCUMENTS 10,555,983 B2    2/2020    Shin et al.
2008/0113043 A1*    5/2008    Seong .................. A61K 36/258
424/728

(Continued)

FOREIGN PATENT DOCUMENTS

CN    103283900 A    9/2013
CN    103800371 A    5/2014
(Continued)

OTHER PUBLICATIONS

Ginseng 2012 https://ruralaction.org/wp-content/uploads/2012/07/Ginseng-Identification-PA.pdf.*
(Continued)

*Primary Examiner* — Susan Hoffman
*Assistant Examiner* — Catheryne Chen
(74) *Attorney, Agent, or Firm* — Merchant & Gould P.C.

(57) ABSTRACT

The present specification relates to a composition for preventing, alleviating or treating burnout syndrome, containing a natural extract as an active ingredient. According to one aspect of the present invention, the composition contains a *ginseng* fruit extract, and thus is useful for preventing, treating and alleviating burnout syndrome. In addition, according to one aspect of the present invention, the composition further contains *ginseng* fruit and one or more selected from the group consisting of red *ginseng*, *Angelica gigas*, *Cornus officinalis*, *Cervi parvum corni*, and *Nigella sativa*, so as to maximize the synergistic effect among two or more ingredients, thereby exhibiting excellent effects on the prevention, treatment and alleviation of burnout syndrome. Therefore, there is an advantage of making individuals and society mentally and physically healthy since burnout syndrome can be prevented, treated and alleviated, by using the composition of the present invention.

9 Claims, 1 Drawing Sheet (51) Int. Cl.

| | |
|---|---|
| *A61K 31/455* | (2006.01) |
| *A61K 31/51* | (2006.01) |
| *A61K 31/519* | (2006.01) |
| *A61K 31/525* | (2006.01) |
| *A61K 31/675* | (2006.01) |
| *A61K 31/704* | (2006.01) |
| *A61K 31/7048* | (2006.01) |
| *A61K 33/00* | (2006.01) |
| *A61K 33/06* | (2006.01) |
| *A61K 33/26* | (2006.01) |
| *A61K 33/30* | (2006.01) |
| *A61K 33/42* | (2006.01) |
| *A61K 35/32* | (2015.01) |
| *A61K 36/232* | (2006.01) |
| *A61K 36/40* | (2006.01) |
| *A61K 36/534* | (2006.01) |
| *A61K 36/54* | (2006.01) |
| *A61K 36/64* | (2006.01) |
| *A61K 36/725* | (2006.01) |
| *A61K 36/79* | (2006.01) |

(56) References Cited

U.S. PATENT DOCUMENTS

| | | |
|---|---|---|
| 2016/0051605 A1 | 2/2016 | Shin et al. |
| 2016/0206673 A1* | 7/2016 | Miller .................. A61K 36/23 |

FOREIGN PATENT DOCUMENTS

| | | |
|---|---|---|
| CN | 104095894 A | 10/2014 |
| CN | 104274852 A | 1/2015 |
| KR | 10-2001-0097871 A | 11/2001 |
| KR | 2010048593 A * | 5/2010 |
| KR | 10-2011-0051162 A | 5/2011 |
| KR | 10-1343819 B1 | 12/2013 |
| KR | 10-2014-0069908 A | 6/2014 |
| KR | 10-2014-0095216 A | 8/2014 |
| KR | 10-2014-0120264 A | 10/2014 |
| KR | 10-2015-0051811 A | 5/2015 |

OTHER PUBLICATIONS 2020, https://www.verywellmind.com/stress-and-burnout-symptoms-and-causes-3144516.*
Dragon Herb 2021 https://www.dragonherbs.com/rehmannia-root.*
International Search Report for PCT/KR2016/001326 (May 16, 2016).
Written Opinion for PCT/KR2016/001326 (May 16, 2016).
Weber et al., "Burnout syndrome: a disease of modern societies?," Occup. Med., 50(7):512-517 (Sep. 2000).
Freudenberger, "The Issues of Staff Burnout in Therapeutic Communities," Journal of Psychoactive Drugs, 18(3):247-251 (Jul.-Sep. 1986).
"8E49 Postviral fatigue syndrome", World Health Organization, International Classification of Diseases 11th Revision, Mortality and Morbidity Statistics. Available at: https://icd.who.int/browse11/l-m/en#/http:/id.who.int/icd/entity/129180281.
"QD85 Burn-out", World Health Organization, International Classification of Diseases 11th Revision, Mortality and Morbidity Statistics. Available at: https://icd.who.int/browse11/l-m/en#/http://id.who.int/icd/entity/569175314.
Office Action from Chinese Application No. 201680010107.1, issued Feb. 6, 2020.
M. Adler, "Red ginseng—A Far Eastern "multitalent" in portrait of the daily practice," Arztezeitschrift fur Naturheilverfahren und Regulationsmedizin, 2005, vol. 46, No. 3, pp. 138-145 (abstract).
Office Action from Japanese Application No. 2017-537283, mailed May 26, 2020.

* cited by examiner (A)

(B)

Before intake     30 minutes after intake     7 days after intake

COMPOSITION FOR PREVENTING, ALLEVIATING OR TREATING BURNOUT SYNDROME

This application is a U.S. National Stage Application under 35 U.S.C. § 371 of International Patent Application No. PCT/KR2016/001326 filed Feb. 5, 2016, which claims the benefit of priority to Korean Patent Application No. 10-2015-0022355 filed Feb. 13, 2015, the disclosures of all of which are hereby incorporated by reference in their entireties. The International Application was published in Korean on Aug. 18, 2016 as WO 2016/129902.

TECHNICAL FIELD

The present disclosure relates to a composition for preventing, improving or treating burnout syndrome, which comprises a natural extract as an active ingredient.

BACKGROUND ART

Recently, concerns about burnout syndrome, or a state of sudden physical or mental exhaustion, are increasing. In particular, about 85% of Korean workers, who work for more than 10 hours a day on average, are known to feel the burnout syndrome due to job stresses. The burnout syndrome has severe effects not only on individuals but also on family, coworkers and society. Since it is known to cause sleep disorder, depression, psychological avoidance, cognitive decline and, in extreme cases, suicidal ideation, development of an agent for preventing, improving and treating burnout syndrome is urgent.

REFERENCES OF RELATED ART

Non-Patent Documents

"The Issues of Staff Burnout in Therapeutic Communities," Herbert J. Freudenberger, Pages 247-251, Volume 18, Issue 3, 1986, Journal of Psychoactive Drugs.

DETAILED DESCRIPTION

Technical Problem

The present disclosure is directed to providing a composition for preventing, improving or treating burnout syndrome.

Technical Solution

In an aspect, the present disclosure provides a health food composition for preventing or improving burnout syndrome, which comprises a *ginseng* berry extract as an active ingredient.

In another aspect, the present disclosure provides a pharmaceutical composition for preventing or treating burnout syndrome, which comprises a *ginseng* berry extract as an active ingredient.

In another aspect, the present disclosure provides a health food composition for preventing or improving burnout syndrome or a pharmaceutical composition for preventing or treating burnout syndrome, which further comprises, in addition to a *ginseng* berry extract, an extract of one or more selected from a group consisting of red *ginseng*, Korean angelica, Korean cornel dogwood, deer antler and star anise.

Advantageous Effects

A composition according to an aspect of the present disclosure, which comprises a *ginseng* berry extract, is useful for preventing, improving and treating burnout syndrome. In addition, a composition according to another aspect of the present disclosure, which comprises not only the *ginseng* berry extract but also an extract of one or more selected from a group consisting of red *ginseng*, Korean angelica, Korean cornel dogwood, deer antler and star anise, exhibits excellent effect of preventing, improving and treating burnout syndrome owing to a synergic effect of the two or more ingredients. Accordingly, the composition of the present disclosure can provide mental and physical health to individuals and society by preventing, improving and treating burnout syndrome.

Furthermore, the composition of the present disclosure can improve human health by relieving menstrual pain, improving fatigue, providing mental stability, improving skin condition, improving limb numbness, relieving climacteric symptoms and improving eye health, in addition to preventing, improving and treating burnout syndrome.

BEST MODE

In the present disclosure, "*ginseng*" may refer to Korean *ginseng*, or *Panax ginseng*.

In the present disclosure, an "extract" includes any substance extracted from a natural product, regardless of extraction method, extraction solvent, extracted ingredients or type of the extract. It is used in a broad concept, including any substance that may be obtained by further processing or treating a substance extracted from a natural product. Specifically, the processing or treatment may be further fermenting or enzymatically treating the extract. Accordingly, the term extract is used in a broad concept in the present disclosure, including a fermentation product, a concentrate and a dried product. Specifically, the extract may be a fermentation product in the present disclosure.

In the present disclosure, "*ginseng* berry" may refer to the fruit of *ginseng*. Specifically, it may refer to the fruit of 3- to 5-year-old *ginseng*, more specifically 4-year-old *ginseng*, which ripens for about a week in mid-July. The *ginseng* berry used in the present disclosure is not limited as to how it is obtained. It may be cultivated or purchased commercially.

The *ginseng* berry used in the present disclosure comprises more minerals including vitamins, and ginsenosides than the *ginseng* root commonly used in the art and, in particular, is entirely different in the composition of ginsenosides. More specifically, the *ginseng* berry comprises more protopanaxatriol (PT)-based ginsenosides including ginsenosides Re, Rg1, Rg2, etc. than protopanaxadiol (PD)-based ginsenosides including ginsenosides Rb1, Rb2, Rc, Rd, etc. and, thus, may include remarkably better effect than the *ginseng* root.

In the present disclosure, a "*ginseng* berry extract" includes any substance extracted from *ginseng* berry, regardless of extraction method, extraction solvent, extracted ingredients or type of the extract. It is used in a broad concept, including a substance extracted from *ginseng* berry by treating with heat, an acid, a base, an enzyme, etc. and any substance that may be obtained by further processing or treating the extracted substance. Specifically, the processing or treatment may be further fermenting or enzymatically treating the *ginseng* berry extract. Accordingly, the *ginseng* berry extract of the present disclosure may be a fermentation product. Also, the *ginseng* berry extract of the present disclosure may be specifically an extract of live *ginseng* berry or an extract of a dried product of *ginseng* berry. In the present disclosure, the live *ginseng* berry, the dried product of *ginseng* berry, or any other processed product of *ginseng* berry that may be used for the extraction (e.g., a fermentation product, a dried pulverization product, etc.) may be similar or identical in composition. Accordingly, the live *ginseng* berry, the dried product of *ginseng* berry, or the other processed product of *ginseng* berry, which are similar or identical in composition, may exhibit the same effect disclosed in the present disclosure.

In the present disclosure, the "*ginseng* berry extract" may be obtained by heating extraction, cold precipitation extraction, reflux condensation extraction, ultrasonic extraction, etc. However, any extraction method obvious to those skilled in the art may be employed without limitation. The *ginseng* berry used to prepare the *ginseng* berry extract of the present disclosure may be a dried product of *ginseng* berry, live *ginseng* berry, *ginseng* berry powder, etc. Any substance obtained from live *ginseng* berry may be used without limitation. The *ginseng* berry extract of the present disclosure may be a $C_1$-$C_6$ alcohol extract of *ginseng* berry, specifically an ethanol extract of *ginseng* berry. More specifically, the *ginseng* berry extract of the present disclosure may be an extract obtained by adding a $C_1$-$C_6$ alcohol, specifically ethanol, to *ginseng* berry and then conducting extraction. The *ginseng* berry extract of the present disclosure also includes one obtained by concentrating the extract obtained by extracting with ethanol under reduced pressure. Specifically, the concentration under reduced pressure may be performed at 35-50° C., although not being limited thereto. When the concentration under reduced pressure is performed within the above-described temperature range, superior synergic effect of the various ingredients in the *ginseng* berry extract of the present disclosure is achieved. In this aspect, the concentration under reduced pressure may be performed at specifically 36° C. or higher, 37° C. or higher, 38° C. or higher, 39° C. or higher, 40° C. or higher, 41° C. or higher or 42° C. or higher, and/or 49° C. or lower, 48° C. or lower, 47° C. or lower, 46° C. or lower, 45° C. or lower, 44° C. or lower or 43° C. or lower. Also, the concentration under reduced pressure may be performed at specifically 600 mmHg or higher, 620 mmHg or higher, 640 mmHg or higher, 650 mmHg or higher, 660 mmHg or higher, 680 mmHg or higher, 700 mmHg or higher, 720 mmHg or higher or 740 mmHg or higher, and/or 760 mmHg or lower, 740 mmHg or lower, 720 mmHg or lower, 700 mmHg or lower, 680 mmHg or lower, 660 mmHg or lower, 650 mmHg or lower, 640 mmHg or lower, 620 mmHg or lower or 600 mmHg or lower.

In an aspect of the present disclosure, the *ginseng* berry extract may be obtained by 1) preparing a dried product of *ginseng* berry by harvesting the fruit of live *ginseng* (*Panax ginseng* C.A. Meyer) and drying the pulp and pericarp of *ginseng* berry by sunlight drying or hot air drying after removing the seed and 2) extracting the prepared dried product of *ginseng* berry at room temperature by adding water or an organic solvent (specifically, ethanol) and then conducting concentration under reduced pressure at 40-45° C. and 600-700 mmHg after filtration.

The *ginseng* berry extract of the present disclosure may comprise ginsenoside Rb1, ginsenoside Rb2, ginsenoside Rb3, ginsenoside Rc, ginsenoside Rd, ginsenoside Re, ginsenoside Rg1 or ginsenoside Rg2. However, because the *ginseng* berry extract of the present disclosure comprises various substances including vitamins, minerals and anthocyanins in addition to the ginsenosides, the effect of the composition according to an aspect of the present disclosure is derived from a combination of the various substances not from only a single ginsenoside or a combination of the ginsenosides (e.g., saponins). In addition, because the effect of the composition according to an aspect of the present disclosure is a synergic effect by a combination of the various substances, it is superior in terms of improvement, prevention and treatment of burnout syndrome to that of a single ginsenoside or a combination of the ginsenosides.

The ginsenoside comprised in the *ginseng* berry extract of the present disclosure may consist essentially of ginsenoside Rb1, ginsenoside Rb2, ginsenoside Rb3, ginsenoside Rc, ginsenoside Rd, ginsenoside Re, ginsenoside Rg1 or ginsenoside Rg2. Also, the ginsenoside comprised in the *ginseng* berry extract of the present disclosure may consist of ginsenoside Rb1, ginsenoside Rb2, ginsenoside Rb3, ginsenoside Rc, ginsenoside Rd, ginsenoside Re, ginsenoside Rg1 or ginsenoside Rg2.

In an aspect of the present disclosure, the *ginseng* berry extract may comprise each 0.1-10 wt % of ginsenoside Rb1, ginsenoside Rb2, ginsenoside Rb3, ginsenoside Rc, ginsenoside Rd, ginsenoside Rg1 or ginsenoside Rg2 based on the total weight of the *ginseng* berry extract.

Specifically, the *ginseng* berry extract of the present disclosure may comprise 1.3-3.3 wt % of ginsenoside Rb1 based on the total weight of the *ginseng* berry extract. Within this range, the *ginseng* berry extract of the present disclosure exhibits superior synergic effect of the various ingredients included therein. In this aspect, the *ginseng* berry extract of the present disclosure may contain 1.4 wt % or more, 1.5 wt % or more, 1.6 wt % or more, 1.7 wt % or more or 1.8 wt % or more, and/or 3.2 wt % or less, 3.1 wt % or less, 3.0 wt % or less, 2.9 wt % or less or 2.8 wt % or less of ginsenoside Rb1.

Specifically, the *ginseng* berry extract of the present disclosure may comprise 1.5-3.5 wt % of ginsenoside Rb2 based on the total weight of the *ginseng* berry extract. Within this range, the *ginseng* berry extract of the present disclosure exhibits superior synergic effect of the various ingredients included therein. In this aspect, the *ginseng* berry extract of the present disclosure may comprise 1.6 wt % or more, 1.7 wt % or more, 1.8 wt % or more, 1.9 wt % or more or 2.0 wt % or more and/or 3.4 wt % or less, 3.3 wt % or less, 3.2 wt % or less, 3.1 wt % or less or 3.0 wt % or less of ginsenoside Rb2.

Specifically, the *ginseng* berry extract of the present disclosure may comprise 0.2-1.2 wt % of ginsenoside Rb3 based on the total weight of the *ginseng* berry extract. Within this range, the *ginseng* berry extract of the present disclosure exhibits superior synergic effect of the various ingredients included therein. In this aspect, the *ginseng* berry extract of the present disclosure may comprise 0.2 wt % or more, 0.3 wt % or more, 0.4 wt % or more, 0.5 wt % or more, 0.6 wt % or more or 0.7 wt % or more and/or 1.5 wt % or less, 1.4 wt % or less, 1.3 wt % or less, 1.2 wt % or less, 1.1 wt % or less, 1.0 wt % or less or 0.9 wt % or less of ginsenoside Rb3.

Specifically, the *ginseng* berry extract of the present disclosure may comprise 2.7-4.7 wt % of ginsenoside Rc based on the total weight of the *ginseng* berry extract. Within this range, the *ginseng* berry extract of the present disclosure exhibits superior synergic effect of the various ingredients included therein. In this aspect, the *ginseng* berry extract of the present disclosure may comprise 2.8 wt % or more, 2.9 wt % or more, 3.0 wt % or more, 3.1 wt % or more or 3.2 wt % or more and/or 4.7 wt % or less, 4.6 wt % or less, 4.5 wt % or less, 4.4 wt % or less or 4.3 wt % or less of ginsenoside Rc.

Specifically, the *ginseng* berry extract of the present disclosure may comprise 3.8-5.8 wt % of ginsenoside Rd based on the total weight of the *ginseng* berry extract. Within this range, the *ginseng* berry extract of the present disclosure exhibits superior synergic effect of the various ingredients included therein. In this aspect, the *ginseng* berry extract of the present disclosure may comprise 3.9 wt % or more, 4.0 wt % or more, 4.1 wt % or more, 4.2 wt % or more or 4.3 wt % or more and/or 5.7 wt % or less, 5.6 wt % or less, 5.5 wt % or less, 5.4 wt % or less or 5.3 wt % or less of ginsenoside Rd.

Specifically, the *ginseng* berry extract of the present disclosure may comprise 8.0-30.0 wt % of ginsenoside Re based on the total weight of the *ginseng* berry extract. Within this range, the *ginseng* berry extract of the present disclosure exhibits superior synergic effect of the various ingredients included therein. In this aspect, the *ginseng* berry extract of the present disclosure may comprise 8.0 wt % or more, 8.5 wt % or more, 9.0 wt % or more, 9.5 wt % or more, 10.0 wt % or more, 10.5 wt % or more, 11.0 wt % or more, 11.5 wt % or more, 12.0 wt % or more, 12.5 wt % or more, 12.6 wt % or more, 12.7 wt % or more, 12.8 wt % or more, 12.9 wt % or more, 13.0 wt % or more, 13.1 wt % or more, 13.2 wt % or more, 13.3 wt % or more, 13.4 wt % or more, 13.5 wt % or more, 13.6 wt % or more, 13.7 wt % or more, 13.8 wt % or more, 13.9 wt % or more, 14.0 wt % or more, 15 wt % or more, 20 wt % or more or 25 wt % or more, and/or 30 wt % or less, 25 wt % or less, 20 wt % or less, 19.0 wt % or less, 18.5 wt % or less, 18.0 wt % or less, 17.5 wt % or less, 17.0 wt % or less, 16.5 wt % or less, 16.4 wt % or less, 16.3 wt % or less, 16.2 wt % or less, 16.1 wt % or less, 16.0 wt % or less, 15.9 wt % or less, 15.8 wt % or less, 15.7 wt % or less, 15.6 wt % or less, 15.5 wt % or less, 15.4 wt % or less, 15.3 wt % or less, 15.2 wt % or less, 15.1 wt % or less or 15.0 wt % or less of ginsenoside Re.

Specifically, the *ginseng* berry extract of the present disclosure may comprise 2.2-4.2 wt % of ginsenoside Rg1 based on the total weight of the *ginseng* berry extract. Within this range, the *ginseng* berry extract of the present disclosure exhibits superior synergic effect of the various ingredients included therein. In this aspect, the *ginseng* berry extract of the present disclosure may comprise 2.3 wt % or more, 2.4 wt % or more, 2.5 wt % or more, 2.6 wt % or more or 2.7 wt % or more and/or 4.3 wt % or less, 4.2 wt % or less, 4.1 wt % or less, 4.0 wt % or less or 3.9 wt % or less of ginsenoside Rg1.

Specifically, the *ginseng* berry extract of the present disclosure may comprise 0.5-2.5 wt % of ginsenoside Rg2 based on the total weight of the *ginseng* berry extract. Within this range, the *ginseng* berry extract of the present disclosure exhibits superior synergic effect of the various ingredients included therein. In this aspect, the *ginseng* berry extract of the present disclosure may comprise 0.6 wt % or more, 0.7 wt % or more, 0.8 wt % or more, 0.9 wt % or more or 1.0 wt % or more and/or 2.4 wt % or less, 2.3 wt % or less, 2.2 wt % or less, 2.1 wt % or less or 2.0 wt % or less of ginsenoside Rg2.

Accordingly, the *ginseng* berry extract of the present disclosure may comprise 24.9-80.0 wt % of total ginsenosides based on the total weight of the *ginseng* berry extract. Within this range, the *ginseng* berry extract of the present disclosure exhibits superior synergic effect of the various ingredients included therein.

In this aspect, the *ginseng* berry extract of the present disclosure may comprise 23.0 wt % or more, 24.0 wt % or more, 25.0 wt % or more, 25.5 wt % or more, 26.0 wt % or more, 26.5 wt % or more, 27 wt % or more, 27.5 wt % or more, 28.0 wt % or more, 28.5 wt % or more, 29.0 wt % or more, 29.5 wt % or more, 30.0 wt % or more, 30.5 wt % or more, 31.0 wt % or more, 31.5 wt % or more, 32.0 wt % or more 35 wt % or more, 40 wt % or more, 45 wt % or more, 50 wt % or more, 55 wt % or more, 60 wt % or more, 65 wt % or more, 70 wt % or more, 75 wt % or more or 80 wt % or more and/or 80 wt % or less, 75 wt % or less, 70 wt % or less, 65 wt % or less, 60 wt % or less, 55 wt % or less, 50 wt % or less, 45 wt % or less, 41.0 wt % or less, 40.5 wt % or less, 40 wt % or less, 39.5 wt % or less, 39 wt % or less, 38.5 wt % or less, 38 wt % or less, 37.5 wt % or less, 37 wt % or less, 36.5 wt % or less, 36 wt % or less, 35.5 wt % or less, 35.0 wt % or less, 34.5 wt % or less or 34.0 wt % or less of ginsenosides based on the total weight of the *ginseng* berry extract.

In addition, the ratio PD/PT of PD (protopanaxadiol) ginsenosides (Rb1, Rb2, Rc, Rd) to PT (protopanaxatriol) ginsenosides (Re, Rg1, Rg2) in the *ginseng* berry extract of the present disclosure may be 0.63-1.21. Within this range, the *ginseng* berry extract of the present disclosure exhibits superior synergic effect of the various ingredients included therein. In this aspect, the ratio PD/PT of PD ginsenosides to PT ginsenosides may be 0.1 or greater, 0.15 or greater, 0.2 or greater, 0.25 or greater, 0.3 or greater, 0.35 or greater, 0.4 or greater, 0.45 or greater, 0.5 or greater, 0.55 or greater, 0.6 or greater, 0.61 or greater, 0.62 or greater, 0.63 or greater, 0.64 or greater, 0.65 or greater, 0.69 or greater, 0.7 or greater, 0.73 or greater, 0.75 or greater, 0.8 or greater, 0.85 or greater, 0.9 or greater, 0.95 or greater, 1.0 or greater, 1.05 or greater, 1.1 or greater, 1.15 or greater or 1.2 or greater and/or 1.5 or smaller, 1.3 or smaller, 1.25 or smaller, 1.24 or smaller, 1.23 or smaller, 1.22 or smaller, 1.21 or smaller, 1.20 or smaller, 1.05 or smaller, 1.0 or smaller, 0.95 or smaller, 0.9 or smaller, 0.85 or smaller, 0.8 or smaller, 0.75 or smaller, 0.73 or smaller, 0.7 or smaller, 0.69 or smaller, 0.65 or smaller, 0.6 or smaller, 0.55 or smaller, 0.5 or smaller, 0.45 or smaller, 0.4 or smaller, 0.3 or smaller, 0.2 or smaller or 0.1 or smaller. Specifically, the ratio PD/PT of PD ginsenosides to PT ginsenosides may be 0.64-1.1, 0.65-1.0, 0.66-0.9, 0.67-0.8 or 0.67-0.75.

In addition, the *ginseng* berry extract of the present disclosure may comprise one or more compound selected from a group consisting of an anthocyanin compound, a derivative thereof and a salt thereof. Specifically, the anthocyanin compound may comprise one or more selected from a group consisting of malvidin chloride, ideain chloride, pelargonidin chloride and keracyanin chloride.

In an aspect of the present disclosure, the *ginseng* berry extract may comprise 8.0-16.0 ppm (w/w) of malvidin chloride, 1.0-5.0 ppm (w/w) of ideain chloride, 6.0-12.0 ppm (w/w) of pelargonidin chloride and 2.0-6.0 ppm (w/w) of keracyanin chloride based on the total weight of the *ginseng* berry extract.

In an aspect of the present disclosure, the *ginseng* berry extract may comprise 8.0 ppm (w/w) or more, 9.0 ppm (w/w) or more, 10.0 ppm (w/w) or more, 11.0 ppm (w/w) or more, 12.0 ppm (w/w) or more, 12.5.0 ppm (w/w) or more, 13.0 ppm (w/w) or more, 14.0 ppm (w/w) or more, 15.0 ppm (w/w) or more or 16.0 ppm (w/w) or more and/or 16.0 ppm (w/w) or less, 15.0 ppm (w/w) or less, 14.0 ppm (w/w) or less, 13.0 ppm (w/w) or less, 12.5 ppm (w/w) or less, 12.0 ppm (w/w) or less, 11.0 ppm (w/w) or less, 10.0 ppm (w/w) or less, 9.0 ppm (w/w) or less or 8.0 ppm (w/w) or less of malvidin chloride based on the total weight of the *ginseng* berry extract.

In an aspect of the present disclosure, the *ginseng* berry extract may comprise 0.1 ppm (w/w) or more, 1.0 ppm (w/w) or more, 2.0 ppm (w/w) or more, 2.2 ppm (w/w) or more, 2.4 ppm (w/w) or more, 2.5 ppm (w/w) or more, 3.0 ppm (w/w) or more, 4.0 ppm (w/w) or more or 5.0 ppm (w/w) or more and/or 5.0 ppm (w/w) or less, 4.0 ppm (w/w) or less, 3.0 ppm (w/w) or less, 2.5 ppm (w/w) or less, 2.4 ppm (w/w) or less, 2.2 ppm (w/w) or less, 2.0 ppm (w/w) or less, 1.0 ppm (w/w) or less or 0.1 ppm (w/w) or less of ideain chloride based on the total weight of the *ginseng* berry extract.

In an aspect of the present disclosure, the *ginseng* berry extract may comprise 6.0 ppm (w/w) or more, 7.0 ppm (w/w) or more, 7.5 ppm (w/w) or more, 8.0 ppm (w/w) or more, 8.5 ppm (w/w) or more, 9.0 ppm (w/w) or more, 10.0 ppm (w/w) or more, 11.0 ppm (w/w) or more or 12.0 ppm (w/w) or more and/or 12.0 ppm (w/w) or less, 11.0 ppm (w/w) or less, 10.0 ppm (w/w) or less, 9.0 ppm (w/w) or less, 8.5 ppm (w/w) or less, 8.0 ppm (w/w) or less, 7.5 ppm (w/w) or less, 7.0 ppm (w/w) or less or 6.0 ppm (w/w) or less of pelargonidin chloride based on the total weight of the *ginseng* berry extract.

In an aspect of the present disclosure, the *ginseng* berry extract may comprise 2.0 ppm (w/w) or more, 2.5 ppm (w/w) or more, 3.0 ppm (w/w) or more, 3.5 ppm (w/w) or more, 4.0 ppm (w/w) or more, 5.0 ppm (w/w) or more or 6.0 ppm (w/w) or more and/or 6.0 ppm (w/w) or less, 5.0 ppm (w/w) or less, 4.0 ppm (w/w) or less, 3.5 ppm (w/w) or less, 3.0 ppm (w/w) or less, 2.5 ppm (w/w) or less or 2.0 ppm (w/w) or less of keracyanin chloride based on the total weight of the *ginseng* berry extract.

In the present disclosure, "burnout syndrome", also called exhaustion syndrome, refers to one of stress-related syndromes caused by hypersensitive reactions to various stress factors. In 1974, Freudenberger defined it as 'the state of fatigue or frustration as a result of failure to receive expected reward in spite of devoted efforts'. The burnout syndrome is caused by extreme physical and mental fatigue and is characterized not only by lethargy as in simple physical fatigue but also by mental aspects such as self-hatred, dereliction, etc. Therefore, it is considered as a disease distinguished from simple chronic fatigue. Specifically, the burnout syndrome is characterized by the following three factors: emotional exhaustion, i.e., the state emotional depletion that results from failure to satisfy excessive job demands, depersonalization, i.e., negative and cynical emotion toward other people, and reduced personal accomplishment, i.e., feeling worthless at work.

In an aspect, the present disclosure relates to a health food composition for preventing or improving burnout syndrome, which comprises a *ginseng* berry extract as an active ingredient.

In another aspect, the present disclosure relates to a pharmaceutical composition for preventing or treating burnout syndrome, which comprises a *ginseng* berry extract as an active ingredient.

In another aspect, the present disclosure relates to a method of preventing, improving or treating burnout syndrome comprises administering a *ginseng* berry extract or a composition to a subject in need of preventing, improving or treating burnout syndrome, wherein the composition comprises a *ginseng* berry extract.

In another aspect, the present disclosure relates to a use of a *ginseng* berry extract for manufacturing a health food composition for preventing, improving or treating burnout syndrome.

In another aspect, the present disclosure relates to a use of a *ginseng* berry extract for manufacturing a pharmaceutical composition for preventing, improving or treating burnout syndrome.

In another aspect, the present disclosure relates to a *ginseng* berry extract for use in preventing, improving or treating burnout syndrome.

The health food or pharmaceutical composition according to an aspect of the present disclosure may comprise 0.01-70 wt % of a *ginseng* berry extract based on the total weight of the composition. Specifically, the composition according to an aspect of the present disclosure may comprise 0.01 wt % or more, 0.05 wt % or more, 0.1 wt % or more, 1 wt % or more, 5 wt % or more, 10 wt % or more, 15 wt % or more, 20 wt % or more, 30 wt % or more, 40 wt % or more, 45 wt % or more, 50 wt % or more, 55 wt % or more, 60 wt % or more, 65 wt % or more, 70 wt % or more or 80 wt % or more, or 99 wt % or less, 90 wt % or less, 80 wt % or less, 75 wt % or less, 65 wt % or less, 60 wt % or less, 55 wt % or less, 50 wt % or less, 45 wt % or less, 40 wt % or less, 30 wt % or less, 20 wt % or less, 10 wt % or less, 5 wt % or less, 1 wt % or less or 0.1 wt % or less of a *ginseng* berry extract based on the total weight of the composition.

The health food or pharmaceutical composition according to an aspect of the present disclosure may comprise 1.3-3.3 wt % of ginsenoside Rb1, 1.5-3.5 wt % of ginsenoside Rb2, 0.4-1.2 wt % of ginsenoside Rb3, 2.7-4.7 wt % of ginsenoside Rc, 3.8-5.8 wt % of ginsenoside Rd, 12.5-16.5 wt % of ginsenoside Re, 2.2-4.2 wt % of ginsenoside Rg1 or 0.5-2.5 wt % of ginsenoside Rg2 based on the total weight of the composition.

Accordingly, the health food or pharmaceutical composition according to an aspect of the present disclosure may comprise 24.9-41.7 wt % of ginsenosides based on the total weight of the *ginseng* berry extract.

Also, the ratio PD/PT of PD ginsenosides to PT ginsenosides in the health food or pharmaceutical composition according to an aspect of the present disclosure may be 0.63-1.21.

The health food or pharmaceutical composition according to an aspect of the present disclosure may further comprise an extract of one or more selected from a group consisting of red *ginseng*, Korean *angelica*, Korean cornel dogwood, deer antler and star anise.

In the present disclosure, the red *ginseng* may refer to *ginseng* obtained by steaming undried (fresh) *ginseng* and then drying the same.

In the present disclosure, the Korean *angelica* may be one or more selected from a group consisting of *Angelica gigas* Nakai, *Angelica sinensis* and *Angelica acutiloba*. In the present disclosure, the Korean *angelica* may mean the underground part, e.g., root, of Korean *angelica*. Live Korean *angelica*, dried Korean *angelica* or any Korean

*angelica* processed otherwise are included. It may also be in any form, including powder. In addition, the Korean *angelica* in the present disclosure includes a live Korean *angelica* and a Korean *angelica* extract extracted by an extraction method known in the art.

In the present disclosure, the Korean cornel dogwood may mean the aerial part, e.g., fruit, of *Macrocarpium officinale*. Live Korean cornel dogwood, dried Korean cornel dogwood or any Korean cornel dogwood processed otherwise are included. It may also be in any form, including powder. In addition, the Korean cornel dogwood in the present disclosure includes a live Korean cornel dogwood and a Korean cornel dogwood extract extracted by an extraction method known in the art.

In the present disclosure, the deer antler refers to a dried antler of deer.

In the present disclosure, the star anise may mean the octagonal aerial part, e.g., fruit, of *Illirium verum*, an evergreen plant in the family Schisandraceae. Live star anise, dried star anise or any star anise processed otherwise are included. It may also be in any form, including powder. In addition, the star anise in the present disclosure includes a live star anise and a star anise extract extracted by an extraction method known in the art. Instead of the star anise, musk obtained from a gland of musk deer may be used.

The pharmaceutical or health food composition according to an aspect of the present disclosure, which comprises a *ginseng* berry extract or further comprises, in addition to the *ginseng* berry extract, an extract of one or more selected from a group consisting of red *ginseng, Korean angelica*, Korean cornel dogwood, deer antler and star anise, is advantageous in that an excellent effect of preventing, improving and treating burnout syndrome can be achieved as the synergic effect of two or more ingredients is maximized.

The pharmaceutical or health food composition according to an aspect of the present disclosure may comprise each 2.5-7 wt % of an extract of one or more selected from a group consisting of red *ginseng, Korean angelica*, Korean cornel dogwood, deer antler and star anise based on the total weight of the composition. Specifically, the composition according to an aspect of the present disclosure may comprise 0.1 wt % or more, 1 wt % or more, 2 wt % or more, 3 wt % or more, 3.5 wt % or more, 4.0 wt % or more, 4.5 wt % or more, 5 wt % or more, 5.5 wt % or more, 6 wt % or more, 7 wt % or more, or 8 wt % or less, 7 wt % or less, 6 wt % or less, 5.5 wt % or less, 5 wt % or less, 4.5 wt % or less, 4 wt % or less, 3.5 wt % or less, 3 wt % or less, 2 wt % or less, 1 wt % or less or 0.1 wt % or less of a red *ginseng* extract based on the total weight of the composition. Specifically, the composition according to an aspect of the present disclosure may comprise each 0.1 wt % or more, 1 wt % or more, 2 wt % or more, 3 wt % or more, 3.5 wt % or more, 4.0 wt % or more, 4.5 wt % or more, 5 wt % or more, 5.5 wt % or more, 5.6 wt % or more, 5.7 wt % or more, 5.8 wt % or more, 5.9 wt % or more, 6 wt % or more, 7 wt % or more, or 8 wt % or less, 7 wt % or less, 6 wt % or less, 5.9 wt % or less, 5.8 wt % or less, 5.7 wt % or less, 5.6 wt % or less, 5.5 wt % or less, 5 wt % or less, 4.5 wt % or less, 4 wt % or less, 3.5 wt % or less, 3 wt % or less, 2 wt % or less, 1 wt % or less or 0.1 wt % or less of a Korean *angelica*, a Korean cornel dogwood or a star anise extract based on the total weight of the composition. Specifically, the composition according to an aspect of the present disclosure may comprise 0.1 wt % or more, 1 wt % or more, 2 wt % or more, 2.5 wt % or more, 2.6 wt % or more, 2.7 wt % or more, 2.8 wt % or more, 2.9 wt % or more, 3 wt % or more, 3.1 wt % or more, 3.2 wt % or more, 3.3 wt % or more, 3.5 wt % or more, 4.0 wt % or more, 4.5 wt % or more, 5 wt % or more, 5.5 wt % or more, 6 wt % or more, 7 wt % or more, or 8 wt % or less, 7 wt % or less, 6 wt % or less, 5.5 wt % or less, 5 wt % or less, 4.5 wt % or less, 4.0 wt % or less, 3.5 wt % or less, 3.3 wt % or less, 3.2 wt % or less, 3.1 wt % or less, 3 wt % or less, 2.9 wt % or less, 2.8 wt % or less, 2.7 wt % or less, 2.6 wt % or less, 2.5 wt % or less, 2 wt % or less, 1 wt % or less or 0.1 wt % or less of a deer antler extract based on the total weight of the composition.

The pharmaceutical or health food composition according to an aspect of the present disclosure may comprise the extracts of Korean *angelica*, Korean cornel dogwood, deer antler and star anise at a weight ratio of 0.8-1.2:0.8-1.2:0.3-0.7:0.8-1.2. Specifically, the weight ratio of the extracts of Korean *angelica*, Korean cornel dogwood, deer antler and star anise comprised in the composition may be 0.9-1.1:0.9-1.1:0.4-0.6:0.9-1.1 or 0.95-1.05:0.95-1.05:0.45-0.55:0.95-1.05. In an aspect of the present disclosure, the extracts of Korean *angelica*, Korean cornel dogwood, deer antler and star anise may be a mixture having the above weight ratio and the mixture may be freeze-dried by lowering pressure at −70 to −50° C. to 10-100 mmHg and maintaining the pressure for 24-72 hours, specifically for 36-60 hours, more specifically for 44-52 hours, more specifically for 47-49 hours.

The pharmaceutical or health food composition according to an aspect of the present disclosure may further comprise an extract of one or more selected from a group consisting of jujube, peppermint, steamed rehmannia root and cinnamon. These ingredients are added to maximize the effect of star anise. The addition of these ingredients can maximize the synergic effect of the composition of the present disclosure.

The pharmaceutical or health food composition according to an aspect of the present disclosure may comprise each 0.1-5 wt % of an extract of one or more selected from a group consisting of jujube, peppermint, steamed rehmannia root and cinnamon based on the total weight of the composition. Specifically, the composition according to an aspect of the present disclosure may comprise 0.1 wt % or more, 0.5 wt % or more, 1.0 wt % or more, 1.5 wt % or more, 1.8 wt % or more, 1.9 wt % or more, 2.0 wt % or more, 2.1 wt % or more, 2.2 wt % or more, 2.3 wt % or more, 2.4 wt % or more, 2.5 wt % or more, 3.0 wt % or more, 3.5 wt % or more, 4.0 wt % or more, 4.5 wt % or more or 5.0 wt % or more, or 6.0 wt % or less, 5.5 wt % or less, 5.0 wt % or less, 4.5 wt % or less, 4.0 wt % or less, 3.5 wt % or less, 3.0 wt % or less, 2.5 wt % or less, 2.4 wt % or less, 2.3 wt % or less, 2.2 wt % or less, 2.1 wt % or less, 2.0 wt % or less, 1.9 wt % or less, 1.8 wt % or less, 1.5 wt % or less, 1.0 wt % or less, 0.5 wt % or less or 0.1 wt % or less of a jujube or steamed rehmannia root extract based on the total weight of the composition. Specifically, the composition according to an aspect of the present disclosure may comprise 0.01 wt % or more, 0.05 wt % or more, 0.1 wt % or more, 0.15 wt % or more, 0.18 wt % or more, 0.19 wt % or more, 0.20 wt % or more, 0.21 wt % or more, 0.22 wt % or more, 0.23 wt % or more, 0.25 wt % or more, 0.3 wt % or more, 0.5 wt % or more, 1 wt % or more, 2 wt % or more, 3 wt % or more, 4 wt % or more, 5 wt % or more, or 5 wt % or less, 4 wt % or less, 3 wt % or less, 2 wt % or less, 1 wt % or less, 0.5 wt % or less, 0.3 wt % or less, 0.25 wt % or less, 0.23 wt % or less, 0.22 wt % or less, 0.21 wt % or less, 0.20 wt % or less, 0.19 wt % or less, 0.18 wt % or less, 0.15 wt % or less, 0.1 wt % or less, 0.05 wt % or less or 0.01 wt % or less of a peppermint or cinnamon extract based on the total weight of the composition.

The pharmaceutical or health food composition according to an aspect of the present disclosure may comprise the extracts of jujube, peppermint, steamed rehmannia root and cinnamon at a weight ratio of 0.8-1.2:0.05-0.15:0.8-1.2: 0.05-0.15. Specifically, the weight ratio of the extracts of jujube, peppermint, steamed rehmannia root and cinnamon comprised in the composition may be 0.9-1.1:0.08-0.12:0.9-1.1:0.08-0.12 or 0.95-1.05:0.09-0.11:0.95-1.05:0.09-0.11. In an aspect of the present disclosure, the extracts of jujube, peppermint, steamed rehmannia root and cinnamon may be a mixture having the above weight ratio and the mixture may be freeze-dried by lowering pressure at −70 to −50° C. to 10-100 mmHg and maintaining the pressure for 24-72 hours, specifically for 36-60 hours, more specifically for 44-52 hours, more specifically for 47-49 hours.

In an aspect of the present disclosure, the *ginseng* berry extract may further comprise a vitamin, a mineral and an anthocyanin compound.

In an aspect of the present disclosure, one or more of 4000 mg/100 g or more of potassium, 600 mg/100 g or more of calcium, 40 mg/100 g or more of iron, 150 mg/100 g or more of phosphorus, 250 mg/100 g or more of magnesium and 140 mg/100 g or more of zinc based on the total weight of the *ginseng* berry extract may be comprised as the mineral.

In an aspect of the present disclosure, the *ginseng* berry extract may comprise 4000 mg/100 g to 10 g/100 g of potassium, 600 mg/100 g to 5 g/100 g of calcium, 40 mg/100 g to 1 g/100 g of iron, 150 mg/100 g to 1 g/100 g of phosphorus, 250 mg/100 g to 5 g/100 g of magnesium and 140 mg/100 g to 5 g/100 g of zinc, although not being limited thereto.

In an aspect of the present disclosure, one or more of 150 μg/100 g or more of vitamin A, 8 mg/100 g or more of vitamin $B_1$, 5 mg/100 g or more of vitamin $B_2$, 8 mg/100 g or more of vitamin $B_6$, 3 mg/100 g or more of vitamin C, 180 μg/100 g or more of vitamin K, 3.5 mg/100 g or more of niacin, 4 mg/100 g or more of pantothenic acid and 250 μg/100 g or more of folic acid based on the total weight of the *ginseng* berry extract may be comprised as the vitamin.

In an aspect of the present disclosure, the *ginseng* berry extract may comprise 150 μg/100 g to 20 mg/100 g of vitamin A, 8 mg/100 g to 5 g/100 g of vitamin $B_1$, 5 mg/100 g to 5 g/100 g of vitamin $B_2$, 8 mg/100 g to 5 g/100 g of vitamin $B_6$, 3 mg/100 g to 5 g/100 g of vitamin C, 180 μg/100 g to 20 mg/100 g of vitamin K, 3.5 mg/100 g to 5 g/100 g of niacin, 4 mg/100 g to 5 g/100 g of pantothenic acid and 250 μg/100 g to 20 mg/100 g of folic acid, although not being limited thereto.

In an aspect of the present disclosure, 20 ppm (w/w) or more of an anthocyanidin compound may be comprised based on the total weight of the *ginseng* berry extract. Specifically, in an aspect of the present disclosure, the anthocyanidin compound may be comprised in an amount of 20-1000 ppm, although not being limited thereto.

The pharmaceutical composition according to an aspect of the present disclosure may be prepared into a solid, semisolid or liquid formulation for oral or parenteral administration by adding an inorganic or organic carrier Examples of formulations for oral administration include a tablet, a pill, a granule, a soft or hard capsule, a powder, a fine granule, a dust, an emulsion, a syrup, a pellet, etc. Examples of formulations for parenteral administration include an injection, a drop, an ointment, a lotion, a spray, a suspension, a suppository, etc. The composition according to an aspect of the present disclosure may be formulated easily according to a commonly employed method and may comprise a surfactant, an excipient, a colorant, a fragrance, a preservative, a stabilizer, a buffering agent, a suspending agent or other commonly used adjuvants.

The active ingredient comprised in the composition according to an aspect of the present disclosure may be provided by being mixed with a carrier or being encapsulated in a receptacle-type carrier. When a diluent is used as a carrier, it may be a solid, semisolid or liquid substance which acts as a carrier, excipient or medium for the active ingredient. Examples of an adequate carrier, excipient or diluent include lactose, dextrose, sucrose, sorbitol, mannitol, calcium silicate, cellulose, methyl cellulose, microcrystalline cellulose, polyvinylpyrrolidone, water, methyl hydroxybenzoate, propyl hydroxybenzoate, talc, magnesium stearate or mineral oil. In another aspect of the present disclosure, the composition may further comprise a filler, an antiflocculant, a lubricant, a humectant, a fragrance, an emulsifier, an antiseptic, etc.

The pharmaceutical composition according to an aspect of the present disclosure may be formulated by a method well known in the art so that the active ingredient can be released in an immediate, sustained or controlled manner after being administered to a mammal.

The pharmaceutical composition according to an aspect of the present disclosure may be administered through various routes, including oral, transdermal, subcutaneous, intravenous, intraperitoneal, intramuscular, topical, patch-mediated or iontophoretic routes, although not being limited thereto. In another aspect of the present disclosure, the pharmaceutical composition may be administered topically or orally.

For a mammal, a daily dosage of the active ingredient may be 1-2000 mg/kg body weight, more specifically 1-1800 mg/kg body weight, 1-1500 mg/kg body weight, 1-1000 mg/kg body weight, 1-800 mg/kg body weight, 1-600 mg/kg body weight, 1-400 mg/kg body weight, 1-200 mg/kg body weight, 1-100 mg/kg body weight, 5-100 mg/kg body weight or 5-70 mg/kg body weight, and administration may be made once or several times a day. However, the actual dosage of the active ingredient is determined considering various factors, including particular disease to be treated, administration route, age, sex and body weight of a patient, severity of the disease, etc. Accordingly, the aforementioned administration dosage does not limit the scope of the present disclosure by any means.

A food composition according to an aspect of the present disclosure includes a food additive composition or a health food composition and may be prepared into a tablet, a hard capsule, a soft capsule, a pill, a granule, a drink, a diet bar, a chocolate, a caramel, confectionery, etc. by adding ingredients commonly used in the art. The health food composition may further comprise suitable functional ingredients.

Hereinafter, the present disclosure will be described in detail through examples and test examples. However, the following examples and test examples are for illustrative purposes only and the scope of the present disclosure is not limited by them. Also, it will be apparent that those of ordinary skill in the art can make various changes and modifications within the scope of the present disclosure defined by the appended claims.

[Example 1] Preparation of *Ginseng* Berry Extract

The fruit of live *ginseng* (*Panax ginseng* C.A. Meyer) was harvested. After separating and removing seeds, the juice, pulp and pericarp of the *ginseng* berry were mixed. After extracting at room temperature for 4 hours by adding 3 L of ethanol per 1 kg of the mixture and filtering, 30 g of a *ginseng* berry extract was obtained by concentrating under reduced pressure of 650 mmHg at 45° C.

[Comparative Example 1] Preparation of *Ginseng* Root Extract

A *ginseng* root extract was prepared in a manner similar to Example 1, except that *ginseng* root was used instead of *ginseng* berry.

[Test Example 1] Comparison of Ginsenoside Contents

Each of the *ginseng* berry extract of Example 1 and the *ginseng* root extract of Comparative Example 1 was treated with ether to remove oil-soluble ingredients. After adding butanol (BuOH) and then concentrating, ginsenoside ingredients comprised in the concentrate were analyzed by HPLC. The result is shown in the following Table 1.

TABLE 1

| Ginsenoside ingredients (wt %) | Ginseng berry extract of Example 1 | Ginseng root extract of Comparative Example 1 |
|---|---|---|
| Rb1 | 2.34 | 4.35 |
| Rb2 | 2.50 | 1.2 |
| Rb3 | 0.76 | 0.95 |
| Rc | 3.77 | 5.05 |
| Rd | 4.83 | 1.2 |
| Re | 14.52 | 1.6 |
| Rg1 | 3.20 | 2 |
| Rg2 | 1.50 | 0.35 |
| Total ginsenosides (dry weight) | 33.42 | 16.70 |
| PD/PT ratio | 0.73 | 3.23 |

It was found out that the *ginseng* berry extract of the present disclosure comprises total ginsenosides in larger quantities than the *ginseng* root extract and that the composition of ginsenosides comprised in the *ginseng* berry was quite different from those of the *ginseng* root. It was also found out that the *ginseng* berry extract of the present disclosure comprises more PT (protopanaxatriol)-based ginsenosides including ginsenosides Re, Rg1, Rg2, etc. than PD (protopanaxadiol)-based ginsenosides including ginsenosides Rb1, Rb2, Rc, Rd, etc. Accordingly, it is expected that it will exhibit much superior effect than the *ginseng* root. In addition, because the total ginsenosides comprised in the *ginseng* berry extract of the present disclosure was as little as 33.42%, it can be seen that the effect of the *ginseng* berry extract of the present disclosure is derived from synergic effect of a combination of various substances included in the *ginseng* berry extract, not just from the ginsenosides.

[Test Example 2] Comparison of Mineral Contents

Mineral ingredients including vitamins comprised in each of the *ginseng* berry extract of Example 1 and the *ginseng* root extract of Comparative Example 1 were analyzed. The analysis was made according to the vitamin and mineral analysis methods described in the Korean Food Code, in order to investigate the characteristics of the *ginseng* berry extract of Example 1 as "fruit" distinguished from the *ginseng* root.

TABLE 2

| Ingredients | Ex. 1 | Comp. Ex. 1 | Ingredients | Ex. 1 | Comp. Ex. 1 |
|---|---|---|---|---|---|
| Potassium (mg/100 g) | 5865.57 | 1460 | Magnesium (mg/100 g) | 354.38 | 160 |
| Calcium (mg/100 g) | 819.26 | 340 | Zinc (mg/100 g) | 178.49 | 1.961 |
| Iron (mg/100 g) | 59.31 | 9.804 | Vit. A (μg/100 g, RE) | 213.11 | — |
| Phosphorus (mg/100 g) | 187.17 | 340 | Vit. B$_1$ (mg/100 g) | 12.29 | 0.16 |
| Vit. B$_2$ (mg/100 g) | 8.45 | 0.50 | Vit. B$_6$ (mg/100 g) | 10.50 | — |
| Vit. C (mg/100g) | 4.91 | 6 | Vit. E (mg/100 g, α-TE) | 23.61 | — |
| Vit. K (μg/100 g) | 232.12 | — | Niacin (mg/100 g, NE) | 5.76 | 1.0 |
| Pantothenic acid (mg/100 g) | 5.87 | 0.66 | Folic acid (μg/100 g) | 349.97 | — |

It was found out that the *ginseng* berry extract of the present disclosure comprise more minerals in larger quantities than the *ginseng* root extract. Accordingly, it is expected that it will exhibit much superior effect than the *ginseng* root. In addition, because the *ginseng* berry extract of the present disclosure comprises various minerals in large quantities, in addition to ginsenosides, it can be seen that the effect of the *ginseng* berry extract of the present disclosure is not derived just from the ginsenosides.

[Test Example 3] Analysis of Anthocyanidin Ingredients in *Ginseng* Berry Extract The anthocyanidin ingredients in the *ginseng* berry extract of Example 1 were analyzed quantitatively.

0.5 g of the *ginseng* berry extract of Example 1 was added to an amber flask. After adding 5 mL of 1% hydrochloric acid and shaking sufficiently, 10 mL of methanol was added. After keeping in a refrigerator for 12 hours and then filtering, analysis was made by HPLC. The HPLC (Waters) analysis was made using Mightysil C18 (250×4.6, 5 μm) and using 2% formic acid in DIW (A) and 2% formic acid in ACN (B) as mobile phases under the condition of 90% A->80% A, 20 min->90% A, 25 min->90% A, 30 min. Measurement was made at UV 520 nm.

The anthocyanidins comprised in the *ginseng* berry were quantitatively analyzed using an anthocyanidin kit (ExtraSynthese, France; for detection of malvidin chloride), a cyanidin derivative kit (ExtraSynthese, France; for detection of ideain chloride and keracyanin chloride), standard pelargonidin chloride and standard petunidin chloride. The result is given in Table 3.

TABLE 3

| Ingredients in ginseng berry extract | Unit: ppm (μg/g) |
|---|---|
| Malvidin chloride | 12.17 |
| Ideain chloride (cyanidin-3-O-galactoside) | 2.36 |
| Pelargonidin chloride | 8.28 |
| Keracyanin chloride | 3.29 |
| Total | 26.1 |

It was found out that the *ginseng* berry extract of the present disclosure comprises various anthocyanidins in large quantities in addition to the ginsenosides. Accordingly, it can be seen that the effect of the *ginseng* berry extract of the present disclosure is not derived just from the ginsenosides.

[Example 3] Preparation of Tablet a Comprising *Ginseng* Berry Extract

A 700-mg tablet comprising 50 wt % of the *ginseng* berry extract of Example 1 was prepared (microcrystalline cellulose 35 wt %, HPMC 15 wt %). The tablet was prepared using a table-top tableting machine (Erweka, Germany).

[Example 4-1] Preparation of Red *Ginseng* Extract and Tablet Comprising the Same 1 kg of a dried product of red *ginseng* root (4-year-old) was extracted at room temperature for 4 hours by adding 3 L of ethanol. After filtering, 300 g of red *ginseng* extract was obtained by concentrating at 45° C. under reduced pressure of 650 mmHg.

A 700-mg tablet comprising 50 wt % of the red *ginseng* extract of Example 1 was prepared (microcrystalline cellulose 35 wt %, HPMC 15 wt %). The tablet was prepared using a table-top tableting machine (Erweka, Germany).

[Example 4-2] Preparation of Tablet B Comprising *Ginseng* Berry Extract (1) Preparation of Gongjin-Dan (Korean Traditional Multi-Herbal Medicine)

1) Korean *Angelica* Extract

3 L of ethanol was added to 1 kg of a dried product of Korean *angelica* (Korean). After extracting at room temperature for 4 hours and then filtering, 300 g of a Korean *angelica* extract was obtained by concentrating at 45° C. under reduced pressure of 650 mmHg.

2) Korean Cornel Dogwood Extract

3 L of ethanol was added to 1 kg of a dried product of Korean cornel dogwood (Korean). After extracting at room temperature for 4 hours and then filtering, 300 g of a Korean cornel dogwood extract was obtained by concentrating at 45° C. under reduced pressure of 650 mmHg.

3) Deer Antler Extract 300 g of a dried product of deer antler (Russian) was pulverized.

4) Star Anise Extract

3 L of ethanol was added to 1 kg of a dried product of star anise (Chinese). After extracting at room temperature for 4 hours and then filtering, 300 g of a star anise extract was obtained by concentrating at 45° C. under reduced pressure of 650 mmHg.

A 100-g gongjin-dan was prepared by mixing the prepared extracts of Korean *angelica*, Korean cornel dogwood, deer antler and star anise at a ratio of 1:1:0.5:0.1. The prepared gongjin-dan was prepared into powder by freeze-drying at −60° C. reduced pressure of 50 mmHg for 48 hours.

(2) Preparation of Mixture Comprising Extracts of Jujube, Peppermint, Steamed Rehmannia Root and Cinnamon 1) Jujube Extract 3 L of ethanol was added to 1 kg of a dried product of jujube (Korean). After extracting at room temperature for 4 hours and then filtering, 300 g of a jujube extract was obtained by concentrating at 45° C. under reduced pressure of 650 mmHg.

2) Peppermint Extract

3 L of ethanol was added to 1 kg of a dried product of peppermint (Korean). After extracting at room temperature for 4 hours and then filtering, 300 g of a peppermint extract was obtained by concentrating at 45° C. under reduced pressure of 650 mmHg.

3) Steamed Rehmannia Root Extract

3 L of ethanol was added to 1 kg of a dried product of steamed rehmannia root (Korean). After extracting at room temperature for 4 hours and then filtering, 300 g of a steamed rehmannia root extract was obtained by concentrating at 45° C. under reduced pressure of 650 mmHg.

4) Cinnamon Extract

3 L of ethanol was added to 1 kg of a dried product of cinnamon (Korean).

After extracting at room temperature for 4 hours and then filtering, 300 g of a cinnamon extract was obtained by concentrating at 45° C. under reduced pressure of 650 mmHg.

100 g of a mixture of the four extracts was prepared by mixing the extracts of jujube, peppermint, steamed rehmannia root and cinnamon at a ratio of 1:0.1:1:0.1. The prepared mixture was prepared into powder by freeze-drying at −60° C. reduced pressure of 50 mmHg for 48 hours.

A 1000-mg tablet B comprising 50 wt % of the *ginseng* berry extract of Example 1, 20 wt % of the gongjin-dan, 5 wt % of the red *ginseng* extract of Example 3-1 and 5 wt % of the mixture of the extracts of jujube, peppermint, steamed rehmannia root and cinnamon was prepared (microcrystalline cellulose 10 wt %, HPMC 10 wt %). The tablet was prepared using a table-top tableting machine (Erweka, Germany).

Comparative Example 2

A tablet comprising only ginsenoside Re at a concentration similar to that of ginsenoside Re comprised in the *ginseng* berry extract of Example 1 was prepared. Specifically, a tablet comprising 60 mg of ginsenoside Re and 290 mg of dextrin was prepared. The tablet was prepared using a table-top tableting machine (Erweka, Germany).

[Test Example 2] Evaluation of Effect of Treating, Preventing and Improving Burnout Syndrome In general, a questionnaire as shown in Table 4 is used for diagnosis of burnout syndrome. This Maslach Burnout Inventory (MBI), which quantitatively but relatively evaluates the symptoms of burnout syndrome, was designed in 1981 by Maslach (see http://www.adrenalfatigue.org/burnout-questionnaire).

TABLE 4

| No. | Questions | Score |
|---|---|---|
| 1 | Do you tire more easily? | 1------2------3------4------5 |
| 2 | Do you feel fatigued rather than energetic? | 1------2------3------4------5 |
| 3 | Are people annoying you by telling you "you don't look so good lately"? | 1------2------3------4------5 |
| 4 | Are you working harder and harder but accomplishing less? | 1------2------3------4------5 |
| 5 | Are you increasingly cynical and disenchanted? | 1------2------3------4------5 |

TABLE 4-continued

| No. | Questions | Score |
|---|---|---|
| 6 | Do you often experience unexplained sadness? | 1------2------3------4------5 |
| 7 | Are you forgetting appointments, deadlines or personal possessions more frequently? | 1------2------3------4------5 |
| 8 | Have you become more irritable? | 1------2------3------4------5 |
| 9 | Are you more short-tempered? | 1------2------3------4------5 |
| 10 | Are you more disappointed with people around you? | 1------2------3------4------5 |
| 11 | Are you seeing family members and close friends less frequently? | 1------2------3------4------5 |
| 12 | Are you too busy to do even routine things like make phone calls or read reports or send cards to friends? | 1------2------3------4------5 |
| 13 | Are you experiencing increased physical complaints (aches, pains, headaches, lingering colds)? | 1------2------3------4------5 |
| 14 | Do you feel disoriented when the activity of the day comes to a halt? | 1------2------3------4------5 |

Before conducting experiments, 30 test subjects in 20 s to 50 s were asked to answer the questionnaire of Table 4 and the scores were summed. For each question, they were asked to give a value ranging from 0 to 5 with "0" representing not being true for them and "5" describing them very well. The values given for the 18 questions were summed and averaged for the 30 people. The result is given in Table 5. The test subjects were asked to take the tablets prepared in Comparative Example 2, Example 3, Example 4-1 and Example 4-2 for 2 weeks, twice a day, 2 tablets at a time. Then, they were asked to answer the questionnaire of Table 4 again. The result of summing and averaging their scores is given in Table 5.

TABLE 5

| Before intake | | After intake | | Difference |
|---|---|---|---|---|
| Non-take group (score) | 60 | Non-take group (score) | 59 | 1 |
| Example 3 (score) | 58 | Example 3 (score) | 47 | 11 |
| Example 4-1 (score) | 59 | Example 4-1 (score) | 55 | 4 |
| Example 4-2 (score) | 65 | Example 4-2 (score) | 42 | 23 |
| Comparative Example 2 (score) | 63 | Comparative Example 2 (score) | 56 | 7 |

It was determined whether each test subject has burnout syndrome according to the criterion given in Table 6 (see http://www.adrenalfatigue.org/burnout-questionnaire).

TABLE 6

| 0-25 | You are doing fine. |
|---|---|
| 26-35 | Your stress is starting to show. |
| 36-50 | You are a candidate for burnout. |
| 51-65 | You are burning out. |
| Over 65 | You are in a dangerous place. |

As a result, all the test subjects who were diagnosed with burnout syndrome before the intake of the tablets of Example 3 and Example 4-2 (i.e., the compositions of the present disclosure) showed treatment or improvement to a state of candidates for burnout after the intake. The non-take control group were still burning out after 2 weeks. Accordingly, it can be seen that the burnout syndrome was remarkably improved as a result of intake of the compositions of the present disclosure. In particular, the tablet of Example 4-2 showed better effect of treating and improving burnout syndrome than that of Example 3 comprising the *ginseng* berry extract only due to the synergic effect of various substances.

Also, it was found out that the *ginseng* berry extract according to an aspect of the present disclosure showed better effect of treating and improving burnout syndrome than the red *ginseng* extract of Example 4-1. Although the tablet of Comparative Example 2 comprised ginsenoside Re at a similar level to that of the *ginseng* berry extract of Example 3, the tablet of Example 3 showed better effect of treating and improving burnout syndrome and this effect was more distinguishable when compared with that of Example 4-2. Accordingly, it can be seen that the effect of treating and improving burnout syndrome of the composition according to an aspect of the present disclosure is derived from the synergic effect of a combination of the various substances included in the *ginseng* berry extract, not just from a single active ingredient. This effect was higher for Example 4-2.

[Test Example 3] Evaluation of Effect of Treating, Preventing and Improving Burnout Syndrome The same test subjects as in Test Example 2 were asked if "they find it hard to do leisure activities such as self-development, exercise or personal appointments after work" before conducting experiments. They were asked to give a value ranging from 0 to 5 with "0" representing not being true for them and "5" describing them very well. The test subjects were asked to take the tablets prepared in Example 3 and Example 4-2 for 2 weeks, twice a day, 2 tablets at a time. Then, they were asked to answer the question again. The result of summing and averaging their scores is given in Table 7.

TABLE 7

| Before intake | | After intake | | Difference |
|---|---|---|---|---|
| Non-take group (score) | 4.2 | Non-take group (score) | 4.1 | 0.1 |
| Example 3 (score) | 4.6 | Example 3 (score) | 4.0 | 0.6 |
| Example 4-2 (score) | 4.5 | Example 4-2 (score) | 3.3 | 1.2 |

As a result, all the test subjects who had no mental and physical energy to do leisure activities before the intake of the tablets of Example 3 and Example 4-2 (i.e., the compositions of the present disclosure) showed increased desire and energy to do leisure activities after the intake. Considering that the non-take control group showed no change after 2 weeks, it can be seen that the intake of the compositions of the present disclosure resulted in remarkable improvement in mental and physical state. In particular, the tablet of Example 4-2 showed better effect of increasing energy than that of Example 2 comprising the *ginseng* berry extract only due to the synergic effect of various substances.

[Test Example 4] Evaluation of Effect on Body Balance

The reason why the *ginseng* extract provides better effect when taken together with gongjin-dan and red *ginseng* can be explained by body balancing based on the principle of suseunghwagang (Water energy Up, Fire energy Down), i.e., the fire energy descends and the water energy rises. To confirm this, the change in body temperature of the subjects who took the tablet of Example 4-2 was monitored.

Specifically, the test subjects were divided into two groups and were asked to take the tablet of Example 4-2, one per day. The change in body temperature was measured using a thermal imaging camera before and 30 minutes after the intake for a week. For group A, the change in the temperature of the whole body was monitored. For group B, only the change in the temperature of the hand was monitored. The measurement was made after staying in a room maintained at constant temperature and constant humidity (20-24° C., 40-60% RH) for 30 minutes. The result is given in FIG. 1. The result for the group A is shown in FIG. 1 (A), and the result for the group B is shown in FIG. 1 (B).

Figure 1:
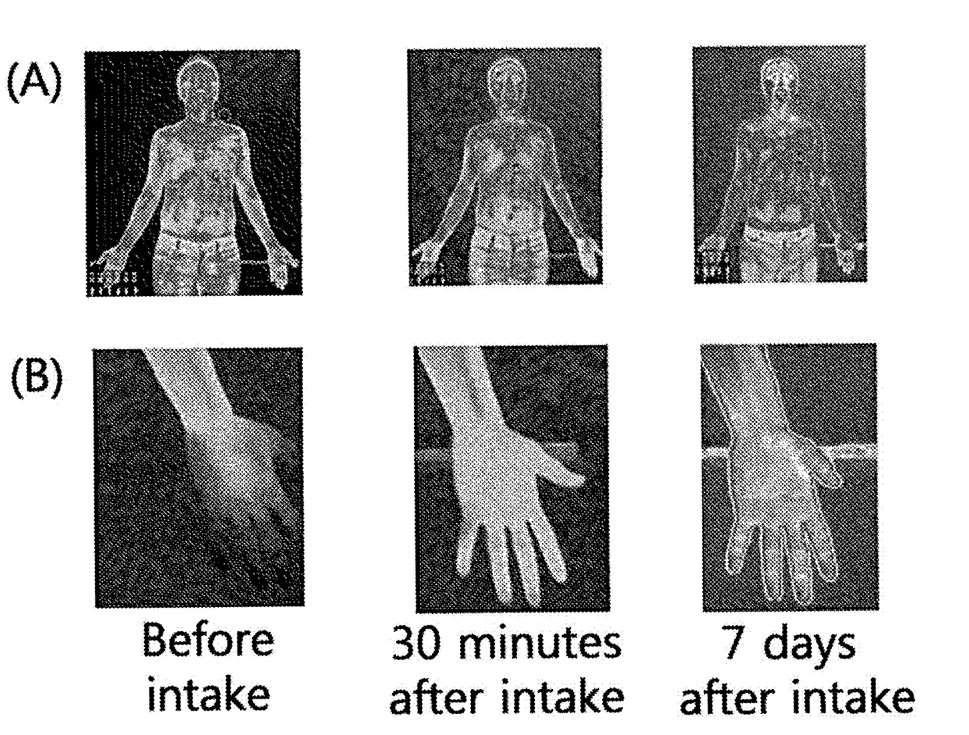
FIG. 1 shows a result of monitoring change in body temperature using a thermal imaging camera after intake of a tablet of Example 4-2 according to an aspect of the present disclosure in order to investigate the change in body balance.

As seen from FIG. 1, it can be seen that steady intake of the tablet of Example 4-2 leads to maintenance of body temperature balance and significant increase in hand temperature based on the suseunghwagang (Water energy Up, Fire energy Down) principle. Specifically, referring to FIG. 1 (A), it can be seen that the body temperature distribution changes from a combination of dark and bright to dark after intake for 7 days. This shows that a uniform body temperature balance is achieved through the suseunghwagang (Water energy Up, Fire energy Down) principle. Also, referring to FIG. 1 (B), it can be seen that the hand temperature rises after intake of the tablet for 7 days, which suggests that blood circulates well to the peripheral blood vessels. Accordingly, it can be seen that the tablet of Example 4-2 according to an aspect of the present disclosure, which comprises the *ginseng* berry extract, gongjin-dan, red *ginseng* and other extracts, improves body balance and blood circulation to peripheral blood vessels. In addition, it provides the effect of improving burnout syndrome.

Hereinafter, the present disclosure will be described in detail through formulation examples. However, other types of formulations are also possible and the scope of the present disclosure is not limited by the formulation examples.

[Formulation Example 1] *Ginseng* Berry 100% Extract

The *ginseng* berry extract of Example 1 was concentrated to a solid content of 60% or higher. After aging at low temperature, a 100% liquid extract was obtained.

[Formulation Example 2] Soft Capsule 1

A soft capsule was prepared according to a commonly employed method by mixing 110 mg of the *ginseng* berry extract of Example 1, 0.8 mg of palm oil, 0.48 mg of hydrogenated vegetable oil, 2.4 mg of yellow beeswax and 3.6 mg lecithin.

[Formulation Example 2] Soft Capsule 2

A soft capsule was prepared according to a commonly employed method by mixing 110 mg of the *ginseng* berry extract of Example 1, 10 mg of a red *ginseng* extract, 12 mg of a Korean *angelica* extract, 12 mg of a Korean cornel dogwood extract, 6 mg of a deer antler extract, 12 mg of a star anise extract, 4 mg of a jujube extract, 0.4 mg of a peppermint extract, 4 mg of a steamed rehmannia root extract, 0.4 mg of a cinnamon extract, 0.8 mg of palm oil, 0.48 mg of hydrogenated vegetable oil, 2.4 mg of yellow beeswax and 3.6 mg lecithin.

[Formulation Example 3] Tablet 1

A tablet was prepared by mixing 160 mg of the *ginseng* berry extract of Example 1, 200 mg of glucose and 196 mg of dextrin, granulating the mixture using a fluidized-bed drier and tableting after adding 7 mg of a sugar ester.

[Formulation Example 3] Tablet 2

A tablet was prepared by mixing 160 mg of the *ginseng* berry extract of Example 1, 15 mg of a red *ginseng* extract, 17 mg of a Korean *angelica* extract, 17 mg of a Korean cornel dogwood extract, 11 mg of a deer antler extract, 17 mg of a star anise extract, 9 mg of a jujube extract, 0.9 mg of a peppermint extract, 9 mg of a steamed rehmannia root extract, 0.9 mg of a cinnamon extract, 200 mg of glucose and 196 mg of dextrin, granulating the mixture using a fluidized-bed drier and tableting after adding 7 mg of a sugar ester.

[Formulation Example 4] Pill 1

A pill was prepared using a pill making machine after mixing 0.9 g of the *ginseng* berry extract of Example 1, 0.3 g of a sugar, 1.91 g of starch and 0.56 g of glycerin.

[Formulation Example 4] Pill 2

A pill was prepared using a pill making machine after mixing 0.9 g of the *ginseng* berry extract of Example 1, 0.09 g of a red *ginseng* extract, 0.09 g of a Korean *angelica* extract, 0.09 g of a Korean cornel dogwood extract, 0.045 g of a deer antler extract, 0.09 g of a star anise extract, 0.03 g of a jujube extract, 0.003 g of a peppermint extract, 0.03 g of a steamed rehmannia root extract, 0.003 g of a cinnamon extract, 0.3 g of a sugar, 1.91 g of starch and 0.56 g of glycerin.

[Formulation Example 5] Granule 1

A granule was prepared by mixing 160 mg of the *ginseng* berry extract of Example 1, 200 mg of glucose and 196 mg of dextrin, granulating using a fluidized-bed drier and filling in a pouch.

[Formulation Example 5] Granule 2

A granule was prepared by mixing 160 mg of the *ginseng* berry extract of Example 1, 10 mg of a red *ginseng* extract, 12 mg of a Korean *angelica* extract, 12 mg of a Korean cornel dogwood extract, 6 mg of a deer antler extract, 12 mg of a star anise extract, 4 mg of a jujube extract, 0.4 mg of a peppermint extract, 4 mg of a steamed rehmannia root extract, 0.4 mg of a cinnamon extract, 200 mg of glucose and 196 mg of dextrin, granulating using a fluidized-bed drier and filling in a pouch.

[Formulation Example 6] Drink 1

110 mg of the *ginseng* berry extract of Example 1, 10 g of glucose and 2 g of citric acid were mixed. After adding 188 g of purified water, 200 mL of the mixture was filled in a bottle. Then, a drink was prepared by sterilizing at 90° C. for 2-3 hours.

[Formulation Example 6] Drink 2

110 mg of the *ginseng* berry extract of Example 1, 10 mg of a red *ginseng* extract, 12 mg of a Korean *angelica* extract, 12 mg of a Korean cornel dogwood extract, 6 mg of a deer antler extract, 12 mg of a star anise extract, 4 mg of a jujube extract, 0.4 mg of a peppermint extract, 4 mg of a steamed rehmannia root extract, 0.4 mg of a cinnamon extract, 10 g of glucose and 2 g of citric acid were mixed. After adding 188 g of purified water, 200 mL of the mixture was filled in a bottle. Then, a drink was prepared by sterilizing at 90° C. for 2-3 hours.

We claim:

1. A method for improving burnout syndrome, comprising:
   administering a composition comprising an effective amount of a *ginseng* berry extract, a red *ginseng* extract, a Korean *angelica* extract, a Korean cornel dogwood extract, a deer antler extract, a star anise extract, a jujube extract, a peppermint extract, a steamed rehmannia root extract and a cinnamon extract to a subject in need thereof,
   wherein the composition comprises 50 wt % of the *ginseng* berry extract, 5 wt % of the red *ginseng* extract, 20 wt % of the Korean *angelica* extract, the Korean cornel dogwood extract, the deer antler extract and the star anise extract, and 5 wt % of the jujube extract, the peppermint extract, the steamed rehmannia root extract and the cinnamon extract based on the total weight of the composition,
   wherein the composition comprises the Korean *angelica* extract, the Korean cornel dogwood extract, the deer antler extract and the star anise extract at a weight ratio of 1:1:0.5:1, and the composition comprises the jujube extract, the peppermint extract, the steamed rehmannia root extract and the cinnamon extract at a weight ratio of 1:0.1:1:0.1,
   wherein the *ginseng* berry extract comprises each 0.1-10 wt % of a ginsenoside Rb1, a ginsenoside Rb2, a ginsenoside Rb3, a ginsenoside Rc, a ginsenoside Rd, a ginsenoside Rg1 or a ginsenoside Rg2 based on the total weight of the composition,
   wherein a ratio of PD ginsenosides to PT ginsenosides in the *ginseng* berry extract is 0.63-1.5, and
   wherein the *ginseng* berry extract comprises 8.0-30.0 wt % of ginsenoside Re based on the total weight of the *ginseng* berry extract.

2. The method according to claim 1, wherein the composition is formulated as a tablet for oral administration, and the tablet is administered twice a day as 2 tablets at a time for more than 7 days.

3. The method according to claim 1, wherein the *ginseng* berry extract comprises 23-80 wt % of total ginsenosides.

4. The method according to claim 1, wherein the *ginseng* berry extract comprises a vitamin, a mineral and an anthocyanidin.

5. The method according to claim 4, wherein the mineral comprises one or more of 4000 mg/100 g or more of a potassium, 600 mg/100 g or more of a calcium, 40 mg/100 g or more of an iron, 150 mg/100 g or more of a phosphorus, 250 mg/100 g or more of a magnesium and 140 mg/100 g or more of a zinc based on the total weight of the *ginseng* berry extract.

6. The method according to claim 4, wherein the vitamin comprises one or more of 150 μg/100 g or more of a vitamin A, 8 mg/100 g or more of a vitamin B1, 5 mg/100 g or more of a vitamin B2, 8 mg/100 g or more of a vitamin B6, 3 mg/100 g or more of a vitamin C, 180 μg/100 g or more of a vitamin K, 3.5 mg/100 g or more of a niacin, 4 mg/100 g or more of a pantothenic acid and 250 μg/100 g or more of a folic acid based on the total weight of the *ginseng* berry extract.

7. The method according to claim 4, wherein the composition comprises 20 ppm (w/w) or more of an anthocyanidin based on the total weight of the *ginseng* berry extract.

8. The method according to claim 4, wherein the anthocyanidin comprises one or more selected from a group consisting of malvidin chloride, ideain chloride, pelargonidin chloride and keracyanin chloride.

9. The method according to claim 8, wherein the *ginseng* berry extract comprises:
   8.0-16.0 ppm (w/w) of malvidin chloride based on the total weight of the *ginseng* berry extract;
   1.0-5.0 ppm (w/w) of ideain chloride based on the total weight of the *ginseng* berry extract;
   3.0-12.0 ppm (w/w) of pelargonidin chloride based on the total weight of the *ginseng* berry extract; and
   2.0-6.0 ppm (w/w) of keracyanin chloride based on the total weight of the *ginseng* berry extract.

* * * * *